United States Patent
Dorman

(10) Patent No.: US 10,219,842 B2
(45) Date of Patent: Mar. 5, 2019

(54) CERVICAL LINK SYSTEM

(75) Inventor: John Dorman, Midland, TX (US)

(73) Assignee: Scapa Flow, LLC, Midland, TX (US)

( * ) Notice: Subject to any disclaimer, the term of this patent is extended or adjusted under 35 U.S.C. 154(b) by 32 days.

(21) Appl. No.: 12/729,990

(22) Filed: Mar. 23, 2010

(65) Prior Publication Data
US 2011/0238115 A1 Sep. 29, 2011

(51) Int. Cl.
*A61B 17/70* (2006.01)

(52) U.S. Cl.
CPC ...... *A61B 17/7059* (2013.01); *A61B 17/7002* (2013.01); *A61B 17/7032* (2013.01); *A61B 17/7041* (2013.01); *A61B 17/7044* (2013.01)

(58) Field of Classification Search
CPC .. A61B 17/70–17/7046; A61B 17/80–17/8095
USPC ................................. 606/246–299
See application file for complete search history.

(56) References Cited

U.S. PATENT DOCUMENTS

| | | | |
|---|---|---|---|
| 5,397,363 A | | 3/1995 | Gelbard |
| 5,704,936 A | * | 1/1998 | Mazel ........................ 606/254 |
| 5,800,435 A | * | 9/1998 | Errico et al. ................. 606/261 |
| 5,843,082 A | * | 12/1998 | Yuan ................. A61B 17/7044 |
| | | | 606/250 |
| 6,117,135 A | * | 9/2000 | Schlapfer ..................... 606/250 |
| 6,206,879 B1 | * | 3/2001 | Marnay .............. A61B 17/7035 |
| | | | 606/53 |
| 6,296,643 B1 | * | 10/2001 | Hopf et al. .................. 606/263 |
| 6,702,817 B2 | * | 3/2004 | Beger et al. ................. 606/86 B |
| 6,786,907 B2 | * | 9/2004 | Lange ........................... 606/250 |
| 6,872,210 B2 | * | 3/2005 | Hearn ............................ 606/71 |
| 7,666,185 B2 | * | 2/2010 | Ryan et al. ..................... 606/71 |
| 8,034,085 B2 | * | 10/2011 | Slivka ................ A61B 17/7022 |
| | | | 606/266 |

(Continued)

FOREIGN PATENT DOCUMENTS

| | | |
|---|---|---|
| FR | 2656214 A1 | 6/1991 |
| WO | WO-9508298 | 3/1995 |

(Continued)

OTHER PUBLICATIONS

International Search Report for Co-Pending PCT Application No. PCT/US11/29651 dated Jun. 2, 2011.

(Continued)

*Primary Examiner* — Nicholas J Plionis
*Assistant Examiner* — Steven J Cotroneo
(74) *Attorney, Agent, or Firm* — Foley & Lardner LLP

(57) ABSTRACT

An adjustable cervical link system that includes a plurality of cervical links for adjustable fixation to articles of a patient's cervical spine, and a connecting assembly having a generally rectangular loop shape defining a substantially open interior therebetween. Each cervical link has a plurality of circular holes each arranged to receive a screw thereby securing the cervical link to the respective article of a patient's cervical spine at a bottom portion of the cervical link. Each cervical link has a plurality of recessed portion along a top portion of the cervical link. Each recessed portion has a generally U-shaped cross-section formed by a bottom portion and a pair of spaced apart side walls. The connecting assembly is arranged to be placed in and frictionally engage the U-shaped cross-section of the recessed portions.

12 Claims, 2 Drawing Sheets

(56) References Cited

U.S. PATENT DOCUMENTS

| | | | |
|---|---|---|---|
| 2002/0193795 A1* | 12/2002 | Gertzbein et al. | 606/61 |
| 2003/0045875 A1* | 3/2003 | Bertranou et al. | 606/61 |
| 2003/0171752 A1* | 9/2003 | Assaker et al. | 606/61 |
| 2003/0220642 A1* | 11/2003 | Freudiger | A61B 17/7005 606/254 |
| 2004/0116931 A1* | 6/2004 | Carlson | A61B 17/7044 606/70 |
| 2005/0228382 A1 | 10/2005 | Richelsoph et al. | |
| 2006/0206114 A1* | 9/2006 | Ensign et al. | 606/61 |
| 2009/0281579 A1* | 11/2009 | Weaver et al. | 606/286 |
| 2010/0004693 A1 | 1/2010 | Miller et al. | |

FOREIGN PATENT DOCUMENTS

| | | |
|---|---|---|
| WO | WO-2008014477 | 1/2008 |
| WO | WO-2010004613 | 1/2010 |

OTHER PUBLICATIONS

Written Opinion for Co-Pending PCT Application No. PCT/US11/29651 dated Jun. 2, 2011.

International Preliminary Report on Patentability for PCT Application No. PCT/US2011/029651, dated Oct. 4, 2012 (8 pages).

\* cited by examiner

CERVICAL LINK SYSTEM

BACKGROUND OF THE INVENTION

Field of the Invention

This invention is related in general to the field of cervical spine devices. More particularly, the invention is related to cervical link system for the cervical spine.

Discussion of the Background

The cervical spine begins at the base of the skull. Seven vertebrae make up the cervical spine with eight pairs of cervical nerves. The individual cervical vertebrae are abbreviated as C1-C7. The related cervical nerves are abbreviated as C1-C8.

Patients who have herniated cervical discs often require surgery. The standard operation for a patient with a herniated cervical disc is an anterior cervical discectomy and fusion (ACDF) operation. ACDF operations have been performed since the 1950s. Back then, the disc was removed from the patient and a bone graft inserted. Later, in the 1970s, surgeons began to use a cervical plate in addition to a bone graft.

There currently exist numerous deficiencies in cervical spine devices that are known in the prior art. For instance, it is difficult to achieve optimum placement of cervical plates due to variations in the size of vertebral bodies in a patient. For example, C5 may be larger than C6, or the C5-C6 disc space may be larger or smaller than the C6-C7 disc space. Further, the insertion of cervical plates that are known in the prior art through small surgical openings is often difficult due to the size of the cervical plate. This is especially true for large cervical plates that are used in multi-level procedures.

Thus, as noted above, there currently exist numerous deficiencies in cervical spine devices that are known in the prior art.

SUMMARY OF THE INVENTION

Accordingly, one aspect of the present invention is to provide an adjustable cervical link system that includes a plurality of cervical links for adjustable fixation to articles of a patient's cervical spine, and a connecting assembly having a generally rectangular loop shape defining a substantially open interior therebetween. Each cervical link has a plurality of circular holes each arranged to receive a screw thereby securing the cervical link to the respective article of a patient's cervical spine at a bottom portion of the cervical link. Each cervical link has a plurality of recessed portion along a top portion of the cervical link. Each recessed portion has a generally U-shaped cross-section formed by a bottom portion and a pair of spaced apart side walls. The connecting assembly is arranged to be placed in and frictionally engage the U-shaped cross-section of the recessed portions.

Another aspect of the present invention is to provide an adjustable cervical link system that includes a plurality of cervical links for adjustable fixation to articles of a patient's cervical spine and a connecting assembly having a generally rectangular loop shape defining a substantially open interior therebetween. Each cervical link has a plurality of circular holes each arranged to receive a screw thereby securing the cervical link to the respective article of a patient's cervical spine at a bottom portion of the cervical link. Each cervical link has an open recessed slot along a top portion of the cervical link, each open recessed slot is defined by a bottom portion and a pair of spaced apart semi-elliptical side walls. A rotatable semi-elliptical adjustment member is positioned within the open recessed slot. The connecting assembly is arranged to be placed in the open recessed slot and to be positioned between the spaced apart semi-elliptical side walls and the rotatable semi-elliptical adjustment member when the rotatable semi-elliptical adjustment member is rotated into a locked position.

BRIEF DESCRIPTION OF THE DRAWINGS

A more complete appreciation of the present invention and many of the attendant advantages thereof will be readily obtained as the same becomes better understood by reference to the following detailed description when considered in conjunction with the accompanying drawings, wherein.

DETAILED DESCRIPTION OF THE PREFERRED EMBODIMENTS

Figure 1:
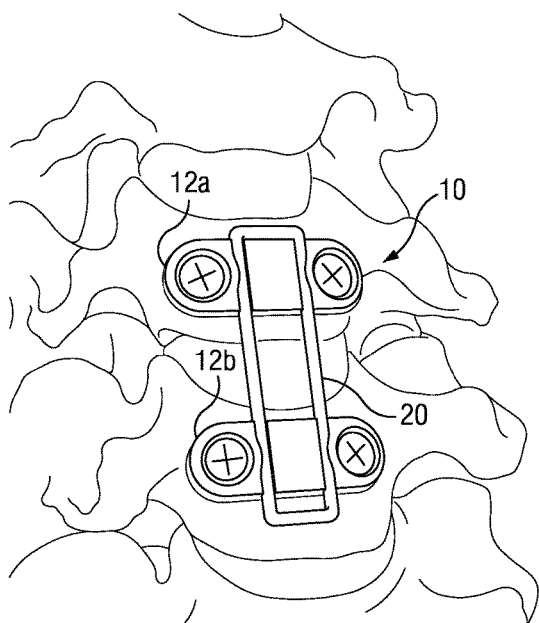
FIG. 1 is a front view of a cervical link system secured to a patient's cervical spine according to an embodiment of the present invention.

Referring now to the drawings, wherein like reference numerals designate identical or corresponding parts throughout the several views, preferred embodiments of the present invention are described.

It is difficult to achieve optimum placement of cervical plates that are known in the prior art due to variations in the size of the vertebral bodies in a patient. For example, C5 may be larger than C6, or the C5-C6 disc space may be larger or smaller than the C6-C7 disc space. Further, the insertion of cervical plates that are known in the prior art through small surgical openings is often difficult due to the size of the cervical plate. This is especially true for large cervical plates that are used in multi-level procedures. The present invention, known as the cervical link system, overcomes these obstacles by allowing each cervical link to be separately secured to a respective vertebral body of a patient. After the cervical links have been secured, the cervical links are then linked together by means of adjustable arms (or connecting assembly) interconnecting the cervical links. The present invention allows for easier placement as the cervical links and adjustable arms (or connecting assembly) due to their small size, which is smaller than cervical plates that are known in the prior art. The adjustable arms (or connecting assembly) interconnecting the cervical links of the present invention allow for possible differences in the size of the vertebral bodies and/or disc spaces in the patient.

Figure 2:
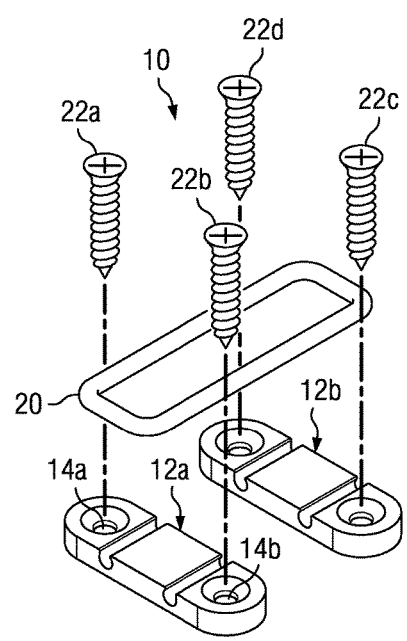
FIG. 2 is an exploded front view of the cervical link system according to an embodiment of the present invention.
Figure 4:
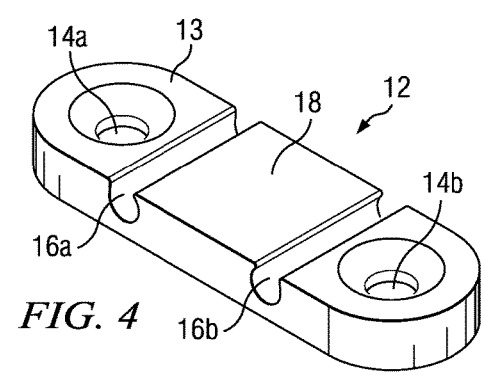
FIG. 4 is a front view of a section of a portion of the cervical link system according to an embodiment of the present invention.

Referring now to FIG. 2, an exploded front view of the cervical link system 10 according to an embodiment of the present invention is shown. As shown in FIG. 1, the cervical link system 10 serves for adjustably connecting vertebral bodies of a patient.

The cervical link system 10 includes one or more cervical links (12a, 12b) and a connecting assembly 20. The connecting assembly 20 is a tubular bar or arm having a generally rectangular loop shape defining an open interior therebetween. Optionally, the connecting assembly 20 may have a generally circular loop shape. Further, the connecting assembly 20 may be two unconnected parallel spaced bars or arms.

Each cervical link (12a, 12b) includes a top portion 13 having circular holes (14a, 14b), and a plurality of circular recessed portions (16a, 16b). Each cervical link (12a, 12b) is secured to a vertebral body of a patient by one or more screws (22a-22d) or the like which are projected through the circular holes (14a, 14b). The connecting assembly 20 is arranged to be inserted into circular recessed portions (16a, 16b) of each cervical link (12a, 12b).

Figure 3:
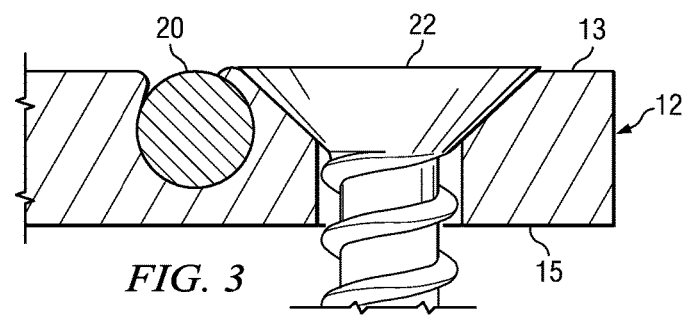
FIG. 3 is an cutaway cross-section view of a portion of the cervical link system according to an embodiment of the present invention.

As shown in FIG. 3, each circular recessed portion (16a, 16b) generally has a semi-circular cross-section configuration defined by side and bottom portions and a generally open top portion along a longitudinal center axis. The generally semi-circular cross-section of the circular recessed portions (16a, 16b) is configured and sized such that the connecting assembly 20 frictionally engages the semi-circular cross-section of the circular recessed portions (16a, 16b) when the connecting assembly 20 is inserted into the circular recessed portions (16a, 16b) of each cervical link (12a, 12b). According to at least one embodiment, of the opening of the top portion of the circular recessed portions (16a, 16b) is slightly less the width of the connecting assembly 20 and configured to deflect slightly during insertion of the connecting assembly 20 and to therefore lock in place the connecting assembly 20 within the circular recessed portions (16a, 16b).

It is of course to be understood that the present invention is not limited to the above identified connecting components and that other connecting components may be used within the scope of the present invention. Each of the cervical link system 10 components may be made from any material. In one embodiment, the components of the cervical link system 10 are made from non-corrosive metal formed from pressure casting or stamping. In another embodiment, the components of the cervical link system 10 are made from plastic, composite, or other suitable material that can be inserted into the body of a patient for an extended period of time without causing medical complications due to composition of such material.

Figure 5:
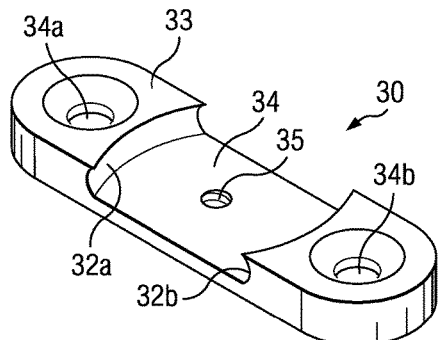
FIG. 5 is a front view of a section of a portion of the cervical link system according to an alternate embodiment of the present invention.
Figure 6:
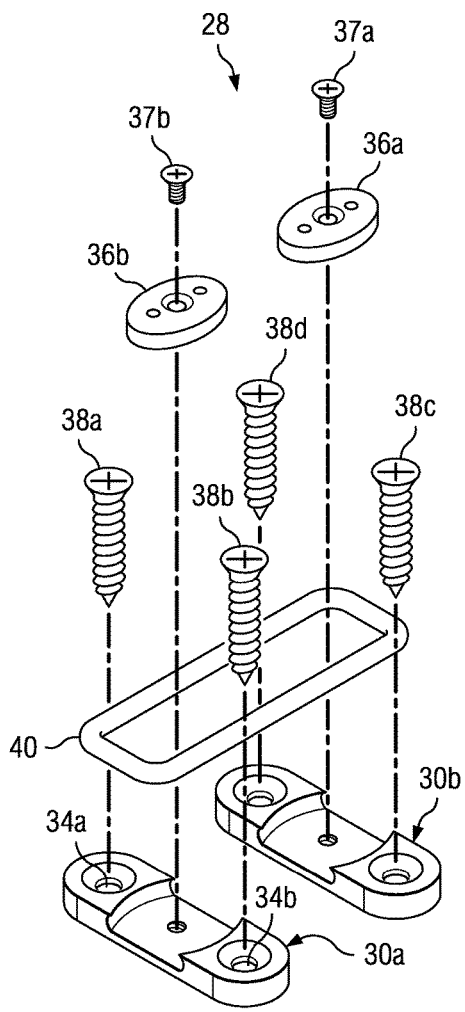
FIG. 6 is an exploded front view of the cervical link system according to an alternate embodiment of the present invention.
Figure 7:
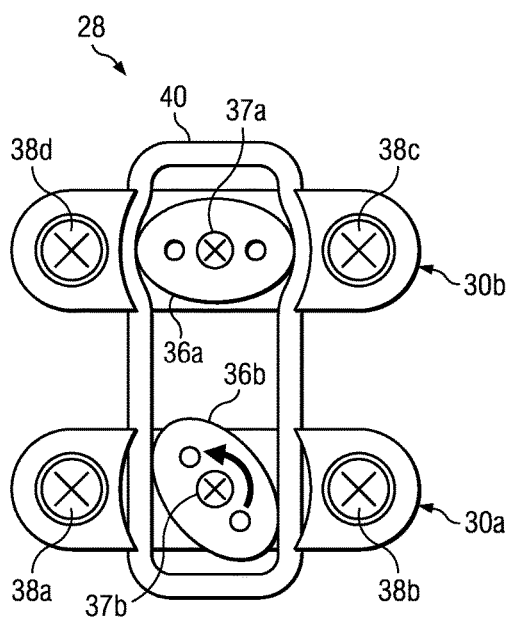
FIG. 7 is a top view of the cervical link system according to an alternate embodiment of the present invention.

Referring now to FIGS. 5-7, a cervical link system 28 according to an alternate embodiment of the present invention is shown. According to this alternate embodiment, the cervical link system 28 includes one or more cervical links (30a, 30b) and a connecting assembly 40. The connecting assembly 40 is a tubular bar or arm having a generally rectangular loop shape defining a substantially open interior therebetween. Optionally, the connecting assembly 40 may have a generally circular loop shape.

Each cervical link (30a, 30b) includes a top portion 33 having circular holes (34a, 34b), and a center recessed portion 34 (or slot) defined by two semi-elliptical side walls and a bottom portion. A semi-elliptical movable locking member 36 is positioned substantially in the center of the center recessed portion 34 by means of any means known in the art, including without limitation, a screw, bar, pin, bolt or the like (37a, 37b). Each semi-elliptical movable locking member (36a, 36b) is rotatably secured to the respective cervical link (30a, 30b) by a screw, bar, pin, bolt or the like (37a, 37b) or the like which are projected through circular holes (35) of the respective cervical link (30a, 30b). It is to be understood that the screws (37a, 37b) and the respective circular holes (35) shown in FIGS. 5-7 are provided for exemplary purposes and that the present invention is not limited to such. Specifically, any other means known in the art may be utilized to rotatably secure the semi-elliptical movable locking member (36a, 36b) to the respective cervical link (30a, 30b), such as a screw, bar, pin, bolt or the like.

The semi-elliptical movable locking member 36 includes a semi-elliptical knob having elongated portions that are configured for frictional engagement with other components of the cervical link system 10 (as detailed below) when the knob is rotated into a locked position.

Each cervical link (30a, 30b) is secured to a vertebral body of a patient, by one or more screws (38a-38d) or the like, which are projected through the circular holes (34a, 34b). The connecting assembly 40 is arranged to be inserted into the center recessed portion 34 along each outer semi-elliptical side wall of the center recessed portion 34 of each cervical link (30a, 30b). The generally semi-circular cross-section of the circular recessed portions (16a, 16b) is configured and sized to receive the connecting assembly 20. The semi-elliptical movable locking member 36 is arranged such that the connecting assembly 40 is frictionally engaged between the outer semi-elliptical side wall of the center recessed portion 34 and the semi-elliptical movable locking member 36 when the semi-elliptical knob of the semi-elliptical movable locking member 36 is rotated such that the elongated portions force the connecting assembly 40 in an outward direction towards the outer semi-elliptical side wall of the center recessed portion 34.

Optionally, semi-elliptical movable locking member 36 may include one or more positioning holes shown to the right and left of its center position. As shown in FIG. 6, exemplary non-limiting countersunk screws (37a, 37b) can be tightened after the knob is rotated into a locked position. The positioning holes may be optionally used by a tool for the purpose of assisting in rotating the knob into a locked position.

During surgery, a vertebral body or disc of a patient is approached anteriorly. An incision is made on the front of the neck, off to the side. The trachea and esophagus are retracted out of the way thereby exposing the vertebral body or disc of the patient. The disc is then removed which decompresses the spinal cord and nerve roots. After the disc is removed, a graft is placed at that location along the vertebral spine of the patient. The graft can be the patient's own bone, but more often is cadaveric bone or a PEEK cage (form of plastic). The type of graft usually depends on surgeon preference. After the graft is placed a cervical link (12a, 12b or 30a, 30b) is selected and screwed into the vertebral body above and below the graft. It is not uncommon to have more than one disc removed during the ACDF. After the cervical links (12a, 12b or 30a, 30b) are attached to the vertebral bodies, the cervical links (12a, 12b or 30a, 30b) are connected by means of frictional engagement (as described above) with the connecting assembly 40.

Although an exemplary embodiment of the system of the present invention has been illustrated in the accompanied drawings and described in the foregoing detailed description, it will be understood that the invention is not limited to the embodiments disclosed, but is capable of numerous rearrangements, modifications, and substitutions without departing from the spirit of the invention as set forth and defined by the following claims. Still further, although depicted in a particular manner, any number of modules and connections can be utilized with the present invention in order to accomplish the present invention, to provide additional known features to the present invention and/or to make the present invention more efficient.

Obviously, many other modifications and variations of the present invention are possible in light of the above teachings. The specific embodiments discussed herein are merely illustrative, and are not meant to limit the scope of the present invention in any manner. It is therefore to be understood that within the scope of the disclosed concept, the invention may be practiced otherwise than as specifically described.

The invention claimed is:

1. An adjustable cervical link system comprising:
    a plurality of cervical links, each cervical link having at least one hole operable to receive a fastener to secure a bottom surface of the cervical link to an article of a cervical spine, wherein each cervical link includes:
        a first recessed portion formed across and within a top surface of the cervical link, the first recessed portion having a first opening in the top surface,
        a second recessed portion formed across and within the top surface of the cervical link, the second recessed portion having a second opening in the top surface, and
        a center member formed between the first opening of the first recessed portion and the second opening of the second recessed portion;
    and
    a connecting assembly including a first member and a second member, the first and second members being substantially rigid, and the first member having a width greater than the first opening of the first recessed portion and the second member having a width greater than the second opening of the second recessed portion,
    wherein at least a portion of the first member is operable to be placed in the first recessed portion, through the first opening, of a first cervical link of the plurality of cervical links and the first recessed portion of a second cervical link of the plurality of cervical links,
    wherein at least a portion of the second member is operable to be placed in the second recessed portion, through the second opening, of the first cervical link and the second recessed portion of the second cervical link,
    wherein at least a portion of at least one of the first or second members are retained within respective first or second recessed portions,
    wherein positions of the plurality of cervical links are adjustable along lengths of the first and second members of the connecting assembly,
    wherein the center members of at least one of the plurality of cervical links is operable to engage an end portion of at least one of the first or second members of the connecting assembly to retain the cervical link in a first position along the lengths of the first and second members of the connecting assembly,
    wherein the engaged end portion of the at least one of the first or second members of the connecting assembly is transverse to the lengths of the first and second members of the connecting assembly,
    wherein the at least one hole of each of the plurality of cervical links is positioned within each of the plurality of cervical links such that application of force to the fastener in a direction toward the article of the cervical spine applies compressive force to a retaining portion of the top surface of the cervical link that defines a portion of at least one of the first opening and the second opening of the respective first or second recessed portions and that retains the portion of at least one of the first or second members such that, in turn, compressive force is applied by the retaining portion to the retained portion of at least one of the first or second members to thereby further retain that portion of at least one of the first or second members.

2. The adjustable cervical link system of claim 1, wherein the first or second recessed portions provides, at least in part, a friction fit for retaining the at least a portion of at least one of the first or second members.

3. The adjustable cervical link system of claim 1, wherein adjusting the positions of the cervical links along the lengths of the first and second members of the connecting assembly includes adjusting a distance between the cervical links in a direction along a length of the respective first and second recessed portions.

4. The adjustable cervical link system of claim 1, wherein the article of the cervical spine comprises a vertebral body.

5. The adjustable cervical link system of claim 1, wherein the first member and second member of the connecting assembly form a shape defining a substantially open interior.

6. The adjustable cervical link system of claim 1, wherein the fastener of each of the plurality of cervical links comprises a fastener head and a fastener body, and:
    wherein the fastener body is to be positioned within the article of the cervical spine; and
    wherein the fastener head is attached to the fastener body, with the fastener head having a width greater than a diameter of the fastener body;
    wherein the at least one hole of each of the plurality of cervical links is positioned such that at least a portion of the fastener head positioned in the at least one hole of that cervical link overlaps with the retained portion of at least one of the first or second members in a direction offset from and parallel to a longitudinal axis of the fastener body.

7. An adjustable cervical link system comprising:
    a first cervical link, the first cervical link comprising:
        at least one hole receiving a first fastener to secure a bottom surface of the first cervical link to a first article of a cervical spine,
        first recessed channels formed across and within a top surface of the first cervical link, the first recessed channels having first openings across the top surface; and
        a center member formed between at least two of the first openings of the first recessed channels;
        wherein the at least one hole is positioned within the first cervical link such that application of force to the first fastener in a direction toward the first article of the cervical spine applies compressive force to a retaining portion adjacent one of the first openings, urging the retaining portion inwardly toward one of the first openings;
    a second cervical link, the second cervical link comprising:
        at least one hole receiving a second fastener to secure a bottom surface of the second cervical link to a second article of the cervical spine,
        second recessed channels formed across and within a top surface of the second cervical link, the second recessed channels having second openings across the top surface; and a center member formed between the second openings of the second recessed channels, and a connecting assembly, the connecting assembly comprising:
- a first portion to be positioned through at least two of the first openings of the first cervical links and within the first recessed channels, wherein at least a portion of the first portion has a width greater than the first openings of the first recessed channels, and
- a second portion to be positioned through at least two of the second openings of the second cervical links and within the second recessed channels, wherein at least a portion of the second portion has a width greater than the second openings of the second recessed channels,
- the first and second portions of the connecting assembly each including an end portion, and
- the first and second portions of the connecting assembly defining at least a portion of an open interior of the connecting assembly, wherein positions of the first and second cervical links are adjustable along a length of the open interior of the connecting assembly, wherein the center members of the first and second cervical links are operable to occupy at least a portion of the open interior of the connecting assembly, wherein the center member of at least one of the first and second cervical links is further operable to engage an interior surface of the end portion of the respective first or second portion of the connecting assembly to retain the at least one of the first and second cervical links in a first position along the length of the open interior of the connecting assembly, and wherein the engaged interior surface of the end portion of the respective first or second portion of the connecting assembly is transverse to the length of the open interior of the connecting assembly.

8. The adjustable cervical link system of claim 7, wherein the at least one of the first recessed channels provides, at least in part, a friction fit for retaining the retained portion of the first portion.

9. The adjustable cervical link system of claim 7, wherein the the at least one of the second recessed channels provides, at least in part, a friction fit for retaining the retained portion of the second portion.

10. The adjustable cervical link system of claim 7, wherein adjusting the positions of the first and second cervical links along the length of the open interior of the connecting assembly includes adjusting a distance between the first cervical link and the second cervical link.

11. The adjustable cervical link system of claim 7, wherein the first and second articles of the cervical spine each comprise a vertebral body.

12. An adjustable cervical link system comprising:
a plurality of cervical links, each cervical link having at least one hole operable to receive a fastener to secure a bottom surface of the cervical link to an article of a cervical spine, wherein each cervical link includes:
- a first recessed portion formed across and within a top surface of the cervical link, the first recessed portion having a first opening in the top surface,
- a second recessed portion formed across and within the top surface of the cervical link, the second recessed portion having a second opening in the top surface, and
- a center member formed between the first opening of the first recessed portion and the second opening of the second recessed portion;

a connecting assembly including a first member and a second member, the first and second members being substantially rigid, and the first member having a width greater than the first opening of the first recessed portion and the second member having a width greater than the second opening of the second recessed portion, wherein at least a portion of the first member is operable to be placed in the first recessed portion, through the first opening, of a first cervical link and the first recessed portion of a second cervical link, wherein at least a portion of the second member is operable to be placed in the second recessed portion, through the second opening, of the first cervical link and the second recessed portion of the second cervical link, wherein at least a portion of at least one of the first or second members are retained within respective first or second recessed portions formed within the top surface of the cervical link by an opening of the respective first or second recessed portions having a width less than a width of the retained portion of the at least one of the first or second members, wherein the at least one hole of each of the plurality of cervical links is positioned within each of the plurality of cervical links such that application of force to the fastener in a direction toward the article of the cervical spine applies compressive force to a retaining portion of the top surface of the cervical link that defines the opening of the respective first or second recessed portions and that retains the portion of at least one of the first or second members such that, in turn, compressive force is applied by the retaining portion to the retained portion of at least one of the first or second members to thereby further retain that portion of at least one of the first or second members, wherein positions of the plurality of cervical links are adjustable along lengths of the first and second members of the connecting assembly, wherein the center members of at least one of the plurality of cervical links is operable to engage an end portion of at least one of the first or second members of the connecting assembly to retain the cervical link in a first position along the lengths of the first and second members of the connecting assembly, and wherein the engaged end portion of the at least one of the first or second members of the connecting assembly is transverse to the lengths of the first and second members of the connecting assembly.

* * * * *